United States Patent
Hasegawa et al.

(10) Patent No.: US 6,706,232 B2
(45) Date of Patent: Mar. 16, 2004

(54) BIOSENSOR

(75) Inventors: Miwa Hasegawa, Hyogo (JP);
Tomohiro Yamamoto, Hirakata (JP);
Motokazu Watanabe, Toyonaka (JP);
Takahiro Nakaminami, Kyoto (JP);
Shin Ikeda, Katano (JP); Toshihiko Yoshioka, Hirakata (JP); Shiro Nankai, Hirakata (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 0 days.

(21) Appl. No.: 10/363,589

(22) PCT Filed: May 17, 2002

(86) PCT No.: PCT/JP02/04826
§ 371 (c)(1),
(2), (4) Date: Mar. 4, 2003

(87) PCT Pub. No.: WO02/095385
PCT Pub. Date: Nov. 28, 2002

(65) Prior Publication Data
US 2003/0183519 A1 Oct. 2, 2003

(51) Int. Cl.[7] .............................................. G01N 27/327
(52) U.S. Cl. ........................... 264/403.09; 204/403.06; 204/403.05
(58) Field of Search ...................... 204/403.05, 403.06, 204/403.09

(56) References Cited

U.S. PATENT DOCUMENTS 5,609,749 A    3/1997   Yamauchi et al.

FOREIGN PATENT DOCUMENTS

| JP | 63-058149 A | 3/1988 |
| JP | 02-062952 A | 3/1990 |
| JP | 2002-202283 A | 7/2002 |
| WO | WO 02/10734 A1 | 2/2002 |
| WO | WO 02/054054 A1 | 7/2002 |

*Primary Examiner*—Alex Noguerola
(74) *Attorney, Agent, or Firm*—Akin Gump Strauss Hauer & Feld, LLP

(57) ABSTRACT

There is provided a cholesterol sensor with high-accuracy and excellent response, whose object to be measured is whole blood, where plasma with hemocytes therein filtered can rapidly reach an electrode system. In a biosensor where plasma with hemocytes therein filtered with a filter is sucked into a sample solution supply pathway due to capillarity, there are formed: a first pressing part for holding a primary side portion of the filter from the bottom; a second pressing part for holding a secondary side portion of the filter from the top and the bottom; a third pressing part for holding the central portion of the filter from the top; and a void for surrounding the filter between the second pressing part and third pressing part.

4 Claims, 4 Drawing Sheets

BIOSENSOR

CROSS-REFERENCE TO RELATED APPLICATION

This application is a Section 371 of International Patent Application No. PCT/JP02/04826, filed May 17, 2002, the disclosure of which is incorporated herein by reference.

TECHNICAL FIELD

The present invention relates to a biosensor, specifically a cholesterol sensor, capable of carrying out speedy, highly-sensitive, simple determination of a specific component in a sample.

BACKGROUND ART

A description will be given to an example of a conventional biosensor in terms of a glucose sensor.

A typical glucose sensor is obtained by forming an electrode system including at least a measurement electrode and a counter electrode on an insulating base plate by a method such as screen printing and then forming an enzyme reaction layer including a hydrophilic polymer, oxidoreductase and an electron mediator on the electrode system. As oxidoreductase used is glucose oxidase; as the electron mediator used is a metal complex, an organic compound or the like, such as potassium ferricyanide, ferrocene derivative or quinone derivative. A buffer is added to the enzyme reaction layer as required.

When a sample solution containing a substrate is added dropwise onto the enzyme reaction layer in this biosensor, the enzyme reaction layer dissolves to cause a reaction of the enzyme with the substrate, which accompanies reduction of the electron mediator. After completion of the enzyme reaction, the substrate concentration in the sample solution can be determined from a value of oxidation current, which is obtained when the reduced electron mediator is electrochemically oxidized.

In this type of glucose sensor, a reductant of the electron mediator generated as a result of the enzyme reaction is oxidized at the electrode, to determine the glucose concentration from the oxidation current value.

Such a biosensor is theoretically capable of measuring diverse substances by using an enzyme whose substrate is an object to be measured. For example, when cholesterol oxidase or cholesterol dehydrogenase is used as oxidoreductase, it is possible to measure a cholesterol value in a serum to be used as a diagnostic indicator in various medical institutions.

Because the enzyme reaction of cholesterol esterase proceeds very slowly, with an appropriate surfactant added thereto, activity of cholesterol esterase can be improved to reduce the time required for the overall reaction.

However, the surfactant, as being included in the reaction system, has an adverse effect on hemocytes, making it impossible to measure whole blood itself, as done in the glucose sensor.

Thereat, a proposal has been made to provide a filter (hemocyte-filtering portion) in the vicinity of an opening of a sample solution supply pathway for rapid supply of only plasma with hemocytes therein filtered, into a sensor. When the filter is inappropriately built in the sensor, however, the hemocytes captured in the filter are destroyed and hemoglobin dissolves out. As hemocyte components get smaller to about the size of the hemoglobin, filtration of the hemocyte components with the filter becomes difficult, whereby the hemoglobin flows into the sample solution supply pathway to cause a measurement error.

This is presumably caused by the fact that a difference in thickness between the filter before absorbing a sample solution and the filter expanded after absorbing the sample solution is not fitted to a gap between pressing parts for holding the filter from the top and the bottom. When the gap between the pressing parts for holding the filter from the top and the bottom is too narrow for the thickness of the filter expanded, the filter is prevented from expanding. The pore size of the filter thus prevented from expanding cannot widen sufficiently, destroying the hemocytes as infiltrating thereinto.

As opposed to this, when the gap between the upper and lower pressing parts is previously set wide for the supposed thickness of the expanded filter, it is feared that the filter may be slided during storage since each sample solution has a different hematocrit value (ratio of red cell volume), resulted from which degrees of expansion of the filter also differ, depending on sample solutions.

Moreover, when a filter is made thinner than a conventional one in order to reduce the amount of a sample solution, mere suction of the sample solution from the termination of a primary side portion of the filter, like a conventional method (Japanese Patent Application No. 2000-399056), reduces the amount of the sample solution that can be absorbed within a certain period of time. For this reason, plasma flows out of a secondary side portion of the filter at a slower rate, and the inside of a sensor, especially the inside of a sample solution supply pathway, is saturated with the plasma at a slower rate, resulting in longer measurement time.

As opposed to this, when a suction area is made wider for increasing the amount of the sample solution that can be absorbed within a certain period of time and then the sample solution is dropped thereonto from the upper part of the filter, the sample solution flows along the surface of the filter at a faster rate than it infiltrates into the filter. The sample solution having flown along the surface of the filter then flows into the sample solution supply pathway from the opening thereof connecting the sample solution supply pathway to the filter, which may lead to a measurement error.

It is an object of the present invention to provide a biosensor improved such that plasma with hemocytes therein filtered reaches an electrode system with rapidity in order to obviate the disadvantages thus described.

It is an object of the present invention to provide a cholesterol sensor with high-accuracy and excellent response, whose object to be measured is whole blood.

DISCLOSURE OF INVENTION

A biosensor of the present invention comprises: an insulating base plate; an electrode system having a working electrode and a counter electrode which are provided on the base plate; a reagent including at least oxidoreductase and an electron mediator; a sample solution supply pathway which includes the electrode system and the reagent and has an air aperture on the termination side thereof; a sample supply part; and a filter which is disposed between the sample solution supply pathway and the sample supply part and filters hemocytes, where plasma with hemocytes therein filtered with the filter is sucked into the sample solution supply pathway due to capillarity, and is characterized by further comprising: a first pressing part for holding a primary side portion of the filter from the bottom; a second pressing part for holding a secondary side portion of the filter from the top and the bottom; a third pressing part for holding the central portion of the filter from the top; and a void for surrounding the filter between the second pressing part and third pressing part.

It is effective that the primary side portion of the filter is exposed outside at the upper face of the biosensor. It is also effective that the secondary side portion of the filter and the working electrode are not in contact with each other.

BEST MODE FOR CARRYING OUT THE INVENTION

Figure 1:
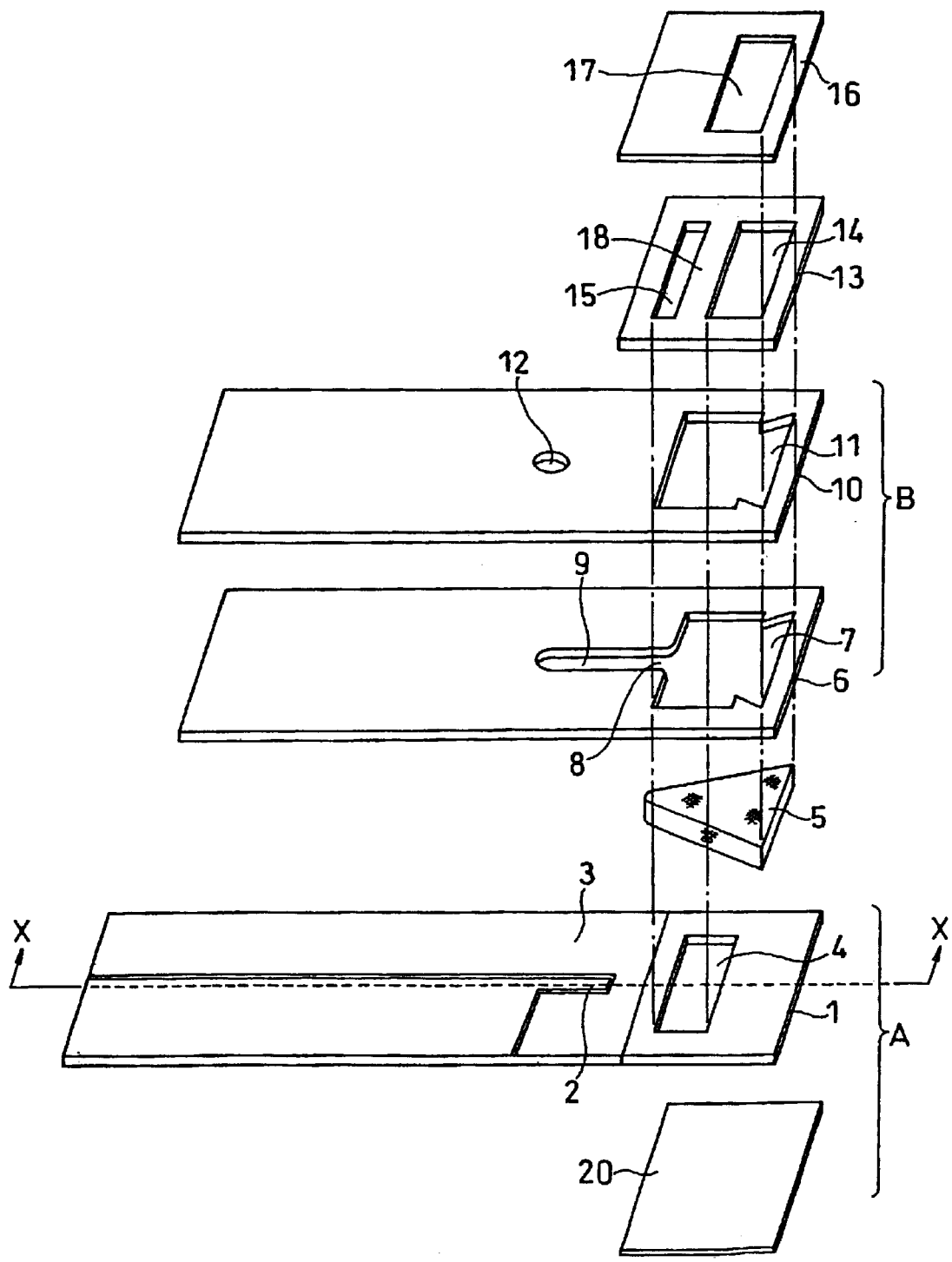
FIG. 1 is an exploded perspective view of a biosensor in accordance with one embodiment of the present invention.

As thus described, the present invention relates to a biosensor comprising: a sample solution supply pathway which includes an electrode system and a reagent and has an air aperture on the termination side thereof; and a filter which is disposed between the sample solution supply pathway and a sample supply part and filters hemocytes, where plasma with hemocytes therein filtered with the filter is sucked into the sample solution supply pathway due to capillarity, and is characterized by further comprising: a first pressing part for holding a primary side portion of the filter from the bottom; a second pressing part for holding a secondary side portion of the filter from the top and the bottom; a third pressing part for holding the central portion of the filter from the top; and a void for surrounding the filter between the second pressing part and third pressing part. This configuration enables prevention of destruction of the hemocytes caused by obstructed expansion of the filter even when a gap between the pressing parts for holding the filter from the top and the bottom is not fitted to the thickness of the filter expanded. Further, dropwise addition of a sample solution directly onto the filter can inhibit a measurement error that may occur as the hemocytes flow along the surface of the filter into the sample solution supply pathway.

In the present description, "a primary side portion" of the filter refers to a portion closer to the sample supply part for supplying the sample while "a secondary side portion" of the filter refers to a portion closer to the sample solution supply pathway where the electrode system is disposed. Further, the base plate side of the filter is referred to as "the bottom" while the opposite side to the base plate of the filter "the top".

Specifically, at the primary side portion of the filter, the first pressing part is in contact only with the bottom side of the filter so that the filter can expand upward when sucking the sample solution. Further, at the central portion of the filter, the third pressing part is in contact only with the top side of the filter so that the filter can expand downward when sucking the sample solution. Moreover, also at the void that exists so as to surround the filter between the second pressing part and the third pressing part, the filter having sucked in the sample solution can expand. In the absence of the void surrounding the filter, there is a possibility that the hemocytes, having transmitted to the part for pressing the filter without passing through the filter, may flow into the electrode system. As thus described, reduction of as many parts that prevent a size change of the filter caused by the expansion thereof, as possible allows free change in pore size of the filter as well as filtration free from the destruction of the hemocytes.

In addition, at the primary side portion of the filter in the biosensor of the present invention, the first pressing part is in contact only with the bottom side of the filter so that an opening can be provided at the upper part to make the primary side portion exposed outside the biosensor, whereby the sample solution can be dropped directly onto the filter.

Furthermore, the third pressing part present on the upper side of the central portion of the filter serves like a weir for preventing the sample solution, dropped from the opening, from flowing along the surface of the upper side of the filter. It is thereby possible to prevent the sample solution from infiltrating into the sample solution supply pathway without undergoing filtration process.

The electron mediator for use in the present invention can be selected from potassium ferricyanide or a redox compound having the electron transferring ability to and from oxidoreductase such as cholesterol oxidase.

Oxidoreductase is an enzyme whose substrate is an object to be measured, and glucose oxidase is applied to a sensor where glucose is the object to be measured. For measurement of a cholesterol value in blood serum to be used as a diagnostic indicator, cholesterol oxidase which is an enzyme for catalyzing an oxidation reaction of cholesterol, or cholesterol esterase which is an enzyme for catalyzing the process of changing cholesterol dehydrogenase and cholesterol ester to cholesterol, is used. Because the enzyme reaction of cholesterol esterase proceeds very slowly, with an appropriate surfactant added thereto, activity of cholesterol esterase can be improved to reduce the time required for the overall reaction.

These are disposed as a reaction layer on or in the vicinity of the electrode system in the sensor. These may also be mixed with a conductive material constituting the electrode and a reagent to form the electrode system. In a sensor which is combined with the base plate provided with the electrode system and comprises a cover member, which forms the sample solution supply pathway for a supply of the sample solution to the electrode system between the base plate and the sensor, these can be provided at the part exposed to the sample solution supply pathway, the opening of the sample solution supply pathway, or the like. Wherever the place is, it is preferable that the sample solution introduced can dissolve the reagent with ease and then arrive at the electrode system. It is preferable to form the hydrophilic polymer layer in contact with the upper face of the electrode system so as to protect the electrode and prevent the reagent formed from being peeled off. Besides the electrode system, it is also preferable that the hydrophilic polymer layer is formed as the base of the reagent as formed or it is included in the bottom-layer reagent.

It is preferable that the layer including the electron mediator is separated from the surfactant for enhancing the solubility. It is also preferable that it is separated from enzyme cholesterol oxidase and cholesterol esterase, which catalyze the oxidation reaction of cholesterol, for the sake of preservation stability.

With respect to a biosensor for measuring a blood sugar level, there is an example where a layer containing lipid is formed so as to cover a layer formed on the electrode system, or the like, to facilitate introduction of the sample solution to the reagent (e.g. Japanese Laid-Open Patent Publication No. 2-062952). In the biosensor for measuring cholesterol in accordance with the present invention, it is preferable to form part of the reagent by freeze-drying (e.g. Japanese Patent Application No. 2000-018834) or to provide hydrophilicity to the surface of a cover member by processing by means of a surfactant, plasma irradiation or the like. Application of such a configuration can eliminate the need for formation of a lipid layer.

The examples of the hydrophilic polymer to be used include water-soluble cellulose derivatives such as, ethyl cellulose, hydroxypropyl cellulose and carboxymethyl cellulose in particular, and polyvinyl pyrrolidone, polyvinyl alcohol, gelatin, agarose, polyacrylic acid and the salts thereof, starch and the derivatives thereof, polymers of maleic anhydride or the salts thereof, polyacrylamide, methacrylate resin, and poly-2-hydroxyethyl methacrylate.

The examples of the surfactant include n-octyl-β-D-thioglucoside, polyethylene glycol monododecyl ether, sodium cholate, dodecyl-β-maltoside, sucrose monolaurate, sodium deoxycholate, sodium taurodeoxycholate, N,N-bis (3-D-gluconeamidopropyl) deoxycholeamide and polyoxyethylene (10) octyl phenyl ether.

As for the lipid favorable used is an amphipathic phospholipid such as lecithin, phosphatidyl choline or phosphatidyl ethanolamine.

As the measuring method of the oxidation current, a two-electrode system composed only of a measurement electrode and a counter electrode and a three-electrode system further comprising a reference electrode are applicable, and in the three-electrode system, more accurate measurement is possible.

In the following, the present invention will be described in detail with the use of concrete embodiments.

FIG. 1 is an exploded perspective view of a biosensor in accordance with a preferred embodiment.

An insulating base plate 1 is made of an insulating resin e.g. polyethylene terephthalate. On the left side part of the base plate 1 in FIG. 1, an electrode system including a working electrode 2 and a counter electrode 3 is formed by forming a palladium thin film by means of vapor deposition or sputtering, followed by laser trimming. The area of the electrode is determined corresponding to a width of a slit 9 formed on a spacer 6 later described. An aperture 4 is formed in the base plate 1.

A spacer 6 to be combined with the base plate 1 comprises an auxiliary slit 7 for accommodating a filter 5 therein, a slit 9 constituting a sample solution supply pathway 9', and an opening 8, through which the auxiliary slit 7 communicates with the slit 9.

In a cover 10 formed are an aperture 11 and an air aperture 12; in an auxiliary plate 13 formed are an aperture 14 for supplying a sample solution to the filter 5, an aperture 15, and a partition portion 18 to serve as a third pressing part.

In an auxiliary upper cover 16 formed is an aperture 17 constituting a sample solution supply part for dropping the sample solution onto the filter 5, and an auxiliary lower cover 20 is composed of a flat plate. In integration of each of the members shown in FIG. 1, the right side part of the auxiliary slit 7, the right side part of the aperture 11 formed in the cover 10, the aperture 14 formed in the auxiliary plate 13 and the aperture 17 formed in the auxiliary upper cover 16 in FIG. 1 are communicated.

The filter (hemocyte-filtering portion) 5 is made of glass-fiber filter paper, and has an isosceles triangle shape with a bottom of 3 mm and a height of 5 mm in the projection thereof drawing to the plane face which is the same as the base plate 1. A semicircular portion with a radius of 0.4 mm (not shown) is formed at the tip of the secondary side portion. The filter 5 has a thickness of about 300 to 400 μm.

For fabrication of this sensor, first, the base plate 1 is placed on an auxiliary lower cover 20 such that the right edge of the auxiliary lower cover 20 is aligned with that of the base plate 1 in such a positional relation shown by the dashed line in FIG. 1 to obtain a joint base plate A.

Next, in such a positional relation shown by the dashed line in FIG. 1, the cover 10 and the spacer 6 are combined such that the respective right sides thereof, namely the parts corresponding to the bottom sides of the isosceles triangle shapes formed in the aperture 11 and the auxiliary slit 7 in the projection thereof drawing to the plane face which is the same as the base plate 1, are aligned with each other, to obtain a joint base plate B. At that time, a reaction layer is formed, as later described, on the part of the cover 10 facing the slit 9, namely on the upper side part of the sample solution supply pathway 9'.

Furthermore, the joint base plate A comprising the base plate 1 and the auxiliary lower cover 20 and the joint base plate B comprising the cover 10 and the spacer 6 are combined in such a positional relation shown by the dashed line in FIG. 1, and in the projection thereof drawing to the plane face which is the same as the base plate 1, the filter 5 is disposed such that the right edge (bottom side) of the primary side portion of the filter 5 having an isosceles triangle shape is aligned with the right end parts of the aperture 11 and the auxiliary slit 7. In other words, the filter 5 is in the state of being disposed on the base plate 1 while being fitted in the auxiliary slit 7 of the space 6 and the aperture 11 of the cover 10.

Moreover, the tip of the secondary side portion of the filter 5 gets into the sample solution supply pathway 9' formed by the slit 9 and is interposed between the base plate 1 and the cover 10, and this interposed part constitutes a second pressing part. A detailed description will be given later. Finally, the auxiliary plate 13 and the auxiliary upper cover 16 are disposed on the cover 10 such that the right ends of the apertures 14 and 17 are aligned with the right ends of the aperture 11 of the cover 10 and the auxiliary slit 7 of the spacer 6 in such a positional relation shown by the dashed line in FIG. 1.

Figure 2:
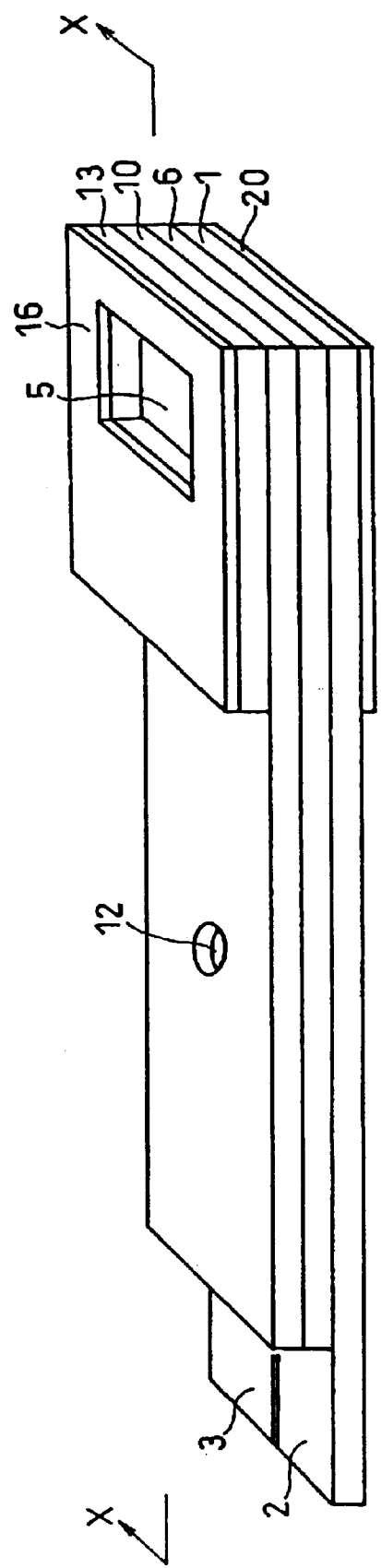
FIG. 2 is a perspective view of a biosensor in accordance with one embodiment of the present invention.
Figure 3:
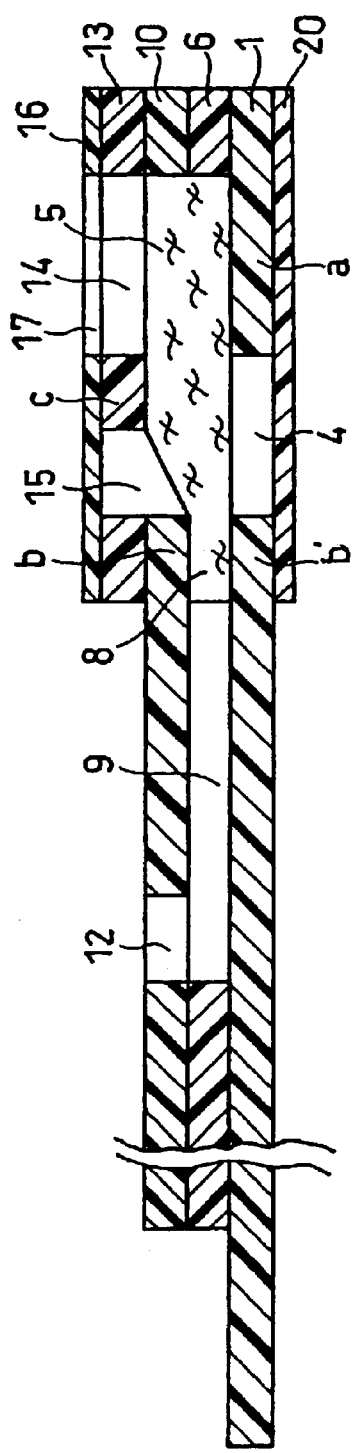
FIG. 3 is a schematic vertical sectional view of the biosensor illustrated in FIG. 2.

A schematic perspective view of the biosensor thus obtained is shown in FIG. 2. The cross sectional structure thereof is shown in FIG. 3. FIG. 3 is a schematic vertical sectional view of the biosensor of the present invention and corresponds to the X—X line cross sectional view shown in FIG. 2. In the biosensor of the present invention shown in FIG. 2, the apertures 15 and 4 for making the filter 5 not in contact with the other members are formed, as shown in FIG. 3.

That is to say, as shown in FIG. 3, there are formed: a first pressing part "a" for holding a primary side portion of the filter 5 from the bottom of the filter 5; second pressing parts "b" and "b'" for holding a secondary side portion of the filter 5 from the top and the bottom of the filter 5; a third pressing part "c" for holding the central portion of the filter 5 from the top; and an aperture (void) 15 for surrounding the filter 5 between the second pressing parts "b" and "b'" and the third pressing part "c". Further, a cavity exists at the part corresponding to the part under the filter 5 as well as under the third pressing part "c", which forms the aperture (void) 4 communicating to the aperture 15.

Figure 4:
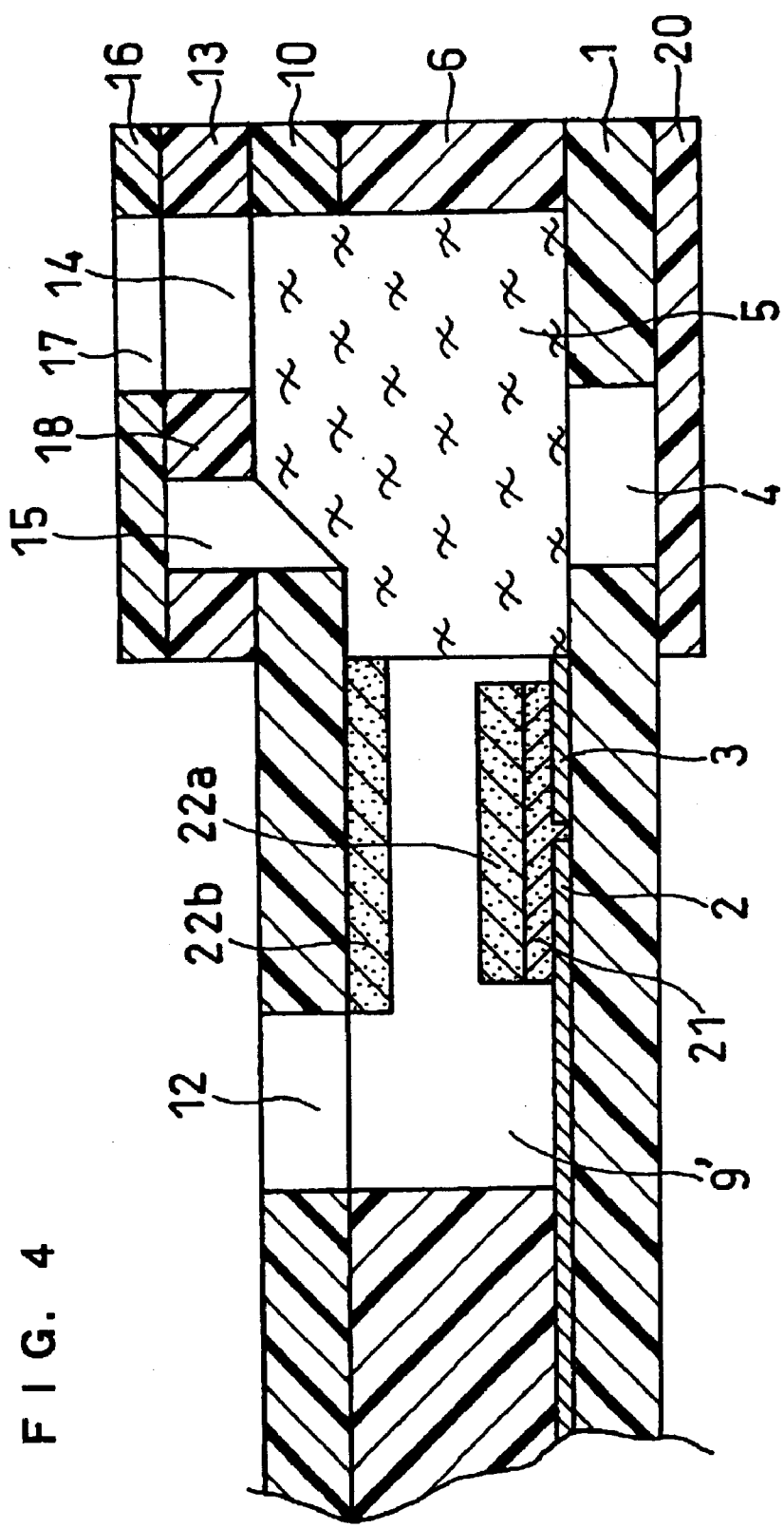
FIG. 4 is an enlarged sectional view of the vicinity of an electrode system of a biosensor in accordance with another embodiment of the present invention.

FIG. 4 is a schematic vertical sectional view showing still another mode of a biosensor of the present invention. A reaction layer and an electrode system are omitted from FIG. 2, whereas the reaction layer and the electrode system are shown in FIG. 4. A hydrophilic polymer layer 21 and a reaction layer 22a are formed on the electrode system (2 and 3) of the base plate 1. Further, a reaction layer 22b is formed on the lower face side of the cover 10 corresponding to the sealing of the sample solution supply pathway. It is to be noted that the other members shown in FIG. 4 are equivalent to those shown in FIG. 3.

While the biosensors shown in FIGS. 1 to 4 are produced using six types of members so as to make the structures thereof easy to understand, the auxiliary upper cover 16 and the auxiliary plate 13, or further including the spacer 10, may be composed of one member. The lower auxiliary cover 20 and the base plate 1 may further be composed of one member.

For measurement of cholesterol in blood with the use of this sensor, blood as the sample solution is supplied from the sample solution supply part constituted by the aperture 17 of the auxiliary upper cover 16 to the part (sample supply part) for holding the filter 5. The blood supplied here infiltrates from the upper surface of the primary side portion of the filter 5 thereinto. In the filter 5, plasma exudes from the termination of the secondary side portion of the filter 5 because the infiltrating rate of hemocytes is slower than that of the plasma which is a liquid component. The exuded plasma then fills the entire sample solution supply pathway 9' constituted by the slit 9 extended to the vicinity of the electrode system and further to the part of the air aperture 12, while dissolving a reaction layer carried on the position covering the electrode system and/or the reverse face of the cover 10. Once the entire sample solution supply pathway 9' is filled with the liquid, the flow of the liquid in the filter 5 also stops and hence the hemocytes are held in the filter 5 at that time, without arriving at the termination of the secondary side portion of the filter 5. It is therefore necessary to design the filter 5 so as to have a difference in flow resistance between the plasma and the hemocytes to the extent that, when the plasma of enough an amount to fill the entire sample solution supply pathway 9' passes through the filter, the hemocytes do not reach the secondary side portion of the filter 5. A depth filter with a pore size of about 1 to 7 μm is favorably applied to the filter of the present invention. In the case of the example of the present invention, the filter favorably has a thickness of 300 to 400 μm.

After undergoing such a process of filtering the hemocytes, a chemical reaction of the reaction layer dissolved by the plasma with a component to be measured (cholesterol in the case of a cholesterol sensor) in the plasma occurs, and a current value in the electrode reaction is measured after a lapse of a certain period of time to determine a component in the plasma.

FIG. 4 shows an example of disposition of the reaction layer in the vicinity of the electrode system of the sample solution supply pathway 9'. On the electrode system of the base plate 1 formed are the hydrophilic polymer layer 21 such as sodium carboxymethyl cellulose (hereinafter simply referred to as "CMC") as well as the reaction layer 22a including a reaction reagent e.g. the electron mediator. The reaction layer 22b including oxidoreductase is formed on the surface exposed to the sample solution supply pathway 9' on the reverse face of the cover member, which is given by combining the cover 10 and the spacer 6.

As shown in FIGS. 1 to 4, the cross sectional area, vertical to the direction of the flowing liquid, of the sample solution supply pathway 9' constituted by the slit 9 is made smaller than the cross sectional area of the primary side portion of the filter 5; however, the part at a distance of 1 mm from the secondary side portion of the filter 5 is compressed and disposed in the vicinity of the opening 8 of the sample solution supply pathway 9'. In the case of suction power of a sensor having the size described in the example of the present invention, the part of the filter 5 to be compressed was favorably at a distance of not longer than about 1 mm from the termination of the secondary side portion. Further, with respect to the degree of compression of the secondary side portion of the filter 5, it was preferably that the secondary side portion was compressed into about one fourth to one third of the primary side portion. While it is difficult to represent the suction power of the sensor by a numeric value in such a compressing condition, in the case of a spacer with a thickness of 100 μm, a filter with a thickness of 370 μm exhibited a favorable measurement result (flow-in rate). It should be noted that, in the case of the filter with a thickness of 310 μm or less, the flow-in rate was slower.

As thus described, making the cross sectional area of the sample solution supply pathway 9' smaller than the cross sectional area of the primary side portion of the filter 5 allows rapid suction of plasma, with hemocytes therein filtered with the filter 5, into the sample solution supply pathway 9' due to capillarity The reaction layer generally comprises an easy-to-dissolve part and a hard-to-dissolve part. A portion of the reaction layer at the edge of the sample solution supply pathway 9', i.e. the part along the wall face of the slit 9 in the spacer 6 is easy to dissolve, whereas the central portion of the reaction layer in the flowing direction of the liquid is hard to dissolve. Since the sample solution having passed through the filter 5 flows along the spacer 6 by priority, there may be cases where the sample solution fills in the air aperture before complete dissolution of the central portion of the reaction layer. Protrusion of the central portion of the secondary side portion of the filter 5 into the sample solution supply pathway 9' more than the both the right and left terminations thereof enables the priority flow of the sample solution through the central portion of the sample solution supply pathway 9', whereby the plasma can be rapidly flown into the sensor without leaving bubbles at the central portion of the sample solution supply pathway 9'.

In-measurement, when blood as the sample solution is supplied from the sample solution supply part constituted by the aperture 17 of the auxiliary upper cover 16 to the filter 5, the blood infiltrates from the upper surface of the primary side portion of the filter 5 thereinto. In the presence of the third pressing part "c" to serve as a partition at that time, dropwise addition of the sample solution onto the surface of the filter 5 will not be followed by priority flowing of the sample solution along the surface of the filter 5 directly into the sample solution supply pathway 9. Further, in the projection thereof drawing to the plane face which is the same as the base plate 1, the position of the third pressing part "c" does not correspond to that of a first pressing part "a", whereby neither the expansion of the filter 5 is obstructed nor there is the fear of destroying the hemocytes.

It is preferable that the electrode system comprises a noble metal electrode. With the width of the sample solution supply pathway being preferably not more than 1.5 mm, accuracy in determination of an electrode area is poor in a printing electrode processed by screen printing. As opposed to this, the noble metal electrode exhibits a high accuracy in determination of the electrode area as being able to be subjected to laser trimming by a width of 0.1 mm.

Below, an example of the present invention will be described; however, the present invention is not limited to this.

EXAMPLE

A cholesterol sensor having the configurations of FIGS. 1 to 4, where the reaction layer 22a included the electron mediator and the reaction layer 22b included cholesterol oxidase, cholesterol esterase and a surfactant, was produced.

First, 5 μl of an aqueous solution containing 0.5 wt % of CMC was dropped onto the electrode system of the base plate 1, and dried in a drying apparatus with warm blast at 50° C. for 10 minutes to form the CMC layer 21.

Next, 4 μl of potassium ferricyanide aqueous solution (corresponding to 70 mM of potassium ferricyanide) was dropped onto the CMC layer 21, and dried in the drying apparatus with warm blast at 50° C. for 10 minutes to form the layer 18a including potassium ferricyanide.

Polyoxyethylene (10) octyl phenyl ether (TritonX100) as the surfactant was added to an aqueous solution with cholesterol oxidase originating from Nocardia (EC1.1.3.6) and cholesterol esterase originating from Pseudomonas (EC.3.1.1.13) dissolved therein. 0.64 μl of this mixed solution was dropped onto the part (sample supply pathway 9') of the slit 9 formed by integrating the cover 10 with the spacer 6, prefrozen with liquid nitrogen at −196° C., and dried in a freeze-drying apparatus for two hours, to form the reaction layer 22b including 570 U/ml of cholesterol oxidase, 1,425 U/ml of cholesterol esterase, and 2 wt % of the surfactant.

The slit 9 had a width of 0.8 mm and a length (the length between the opening of the sample solution supply pathway 9' and the air aperture) of 4.5 mm. The spacer 6 had a thickness (the distance between the base plate 1 and the cover 10) of 100 μm.

As for the filter 5 used is one made of a glass fiber filter having a thickness of about 370 μm in an isosceles triangle shape with a bottom of 3 mm and a height of 5 mm. The tip of the secondary side portion (the part in contact with the opening 8 of the sample solution supply pathway 9') was roundly processed and then placed between the joint base plate A comprising the base plate 1 and the auxiliary lower cover 20 and the joint base plate B comprising the cover 10 and the spacer 6.

Subsequently, the member obtained by placing the filter 5 between the joint base plate A and the joint base plate B was bonded to the member obtained by integrating the auxiliary plate 13 with the auxiliary upper cover 16, to produce a cholesterol sensor having the structures shown in FIGS. 1, 2 and 4.

Figure 5:
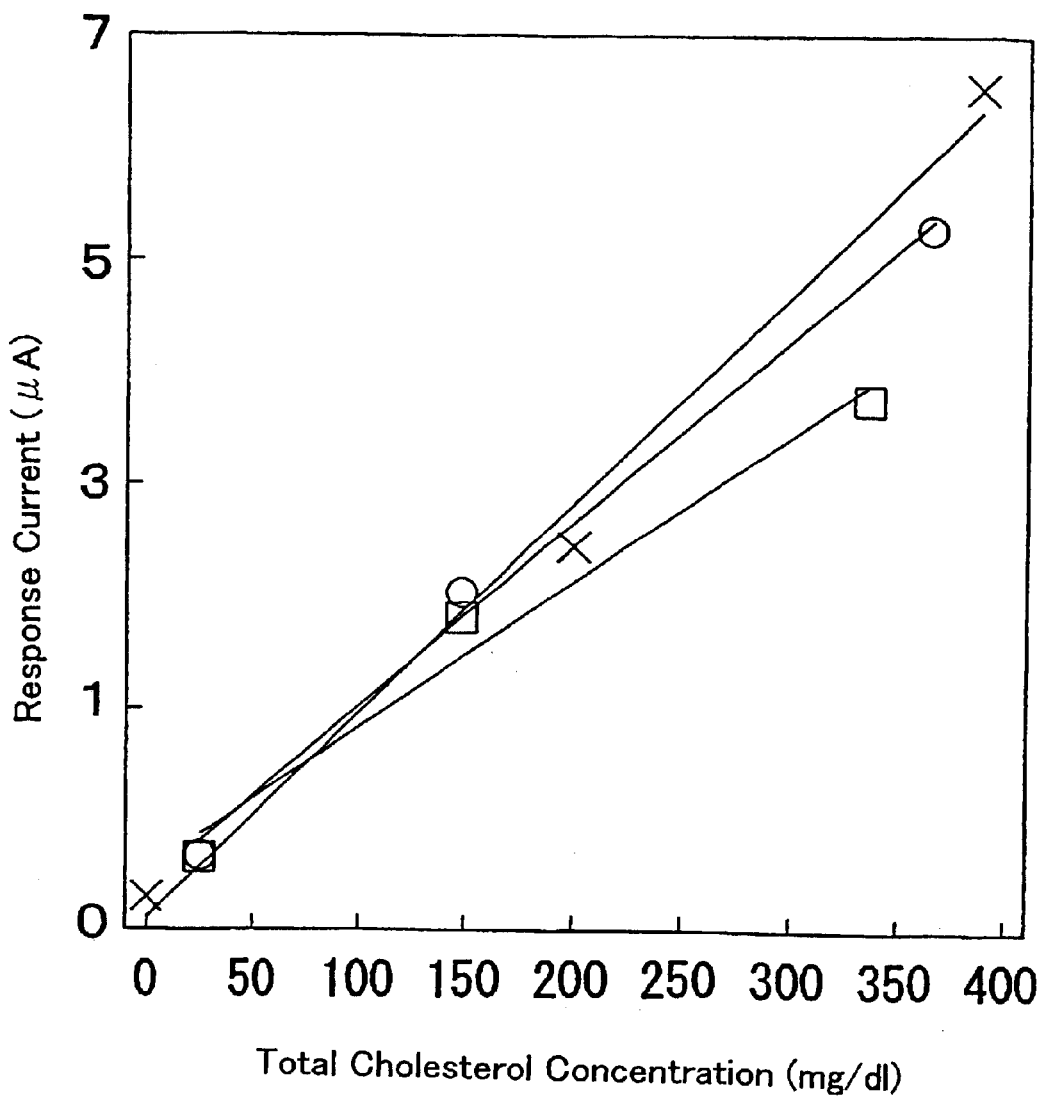
FIG. 5 is a diagram showing a response characteristic of a cholesterol sensor in an example of the present invention.

10 μl of whole blood as the sample solution was introduced into the sample solution supply part of this sensor; three minutes later, a pulse voltage of +0.2 V was applied to the measuring electrode toward the anode relative to the counter electrode, and five seconds later, a value of a current flowing between the working electrode and the counter electrode was measured. The results were shown in FIG. 5. FIG. 5 is a graph showing relations between the total cholesterol concentration and the response current.

As is evident from FIG. 5, according to the sensor of the present invention, a favorable linearity between the cholesterol concentration and the response current value was obtained. In FIG. 5, "×" indicates the result of plasma with a ratio of red cell volume of 0%, "○" indicates the result of whole blood with a ratio of red cell volume of 35%, and "□" indicates the result of whole blood with a ratio of red cell volume of 60%.

Industrial Applicability

According to the present invention, hemocytes as interfering substances can be removed without the destruction thereof by a filter, and plasma with hemocytes therein removed can be supplied with rapidity to an electrode system even with the thickness of the filter being thin. Accordingly, there can be provided a chemical biosensor excellent in response characteristic.

What is claimed is:

1. A biosensor comprising: An insulating base plate; an electrode system having a working electrode and a counter electrode which are provided on said base plate; a reagent including at least oxidoreductase and an electron mediator; a sample solution supply pathway which includes said electrode system and said reagent and has an air aperture on the termination side thereof; a sample supply part; and a filter which is disposed between said sample solution supply pathway and said sample supply part and filters hemocytes, where plasma with hemocytes therein filtered with said filter is sucked into said sample solution supply pathway due to capillarity, characterized by further comprising: a first pressing part for holding a primary side portion of said filter from the bottom; a second pressing port for holding a secondary side portion of said filter from the top and the bottom; a third pressing part for holding the central portion of said filter from the top; and a void for surrounding said filter between said second pressing part and third pressing part.

2. The biosensor in accordance with claim 1, characterized in that said primary side portion of said filter is exposed outside at the upper face of the biosensor.

3. The biosensor in accordance with claim 1, characterized in that said secondary side portion of said filter and said working electrode are not in contact with each other.

4. The biosensor in accordance with claim 2, characterized in that said secondary side portion of said filter and said working electrode are not in contact with each other.

* * * * *